United States Patent
An et al.

(10) Patent No.: US 11,279,391 B2
(45) Date of Patent: Mar. 22, 2022

(54) STEERING WHEEL FOR MEASURING DRIVER BIOLOGICAL PARAMETER

(71) Applicants: HYUNDAI MOTOR COMPANY, Seoul (KR); KIA MOTORS CORPORATION, Seoul (KR)

(72) Inventors: Dae Yun An, Anyang-si (KR); Eung Hwan Kim, Seoul (KR); Gyun Ha Kim, Incheon (KR); Jin Young Koh, Suwon-si (KR); Won Lee, Siheung-si (KR)

(73) Assignees: HYUNDAI MOTOR COMPANY, Seoul (KR); KIA MOTORS CORPORATION, Seoul (KR)

( * ) Notice: Subject to any disclaimer, the term of this patent is extended or adjusted under 35 U.S.C. 154(b) by 0 days.

(21) Appl. No.: 17/096,189

(22) Filed: Nov. 12, 2020

(65) Prior Publication Data
US 2022/0048553 A1   Feb. 17, 2022

(30) Foreign Application Priority Data
Aug. 11, 2020  (KR) .................. 10-2020-0100749

(51) Int. Cl.
| | |
|---|---|
| *B62D 1/04* | (2006.01) |
| *B62D 1/06* | (2006.01) |
| *B60R 16/027* | (2006.01) |
| *B62D 1/08* | (2006.01) |
| *A61B 5/00* | (2006.01) |
| *B62D 1/10* | (2006.01) |
| *A61B 5/024* | (2006.01) |

(Continued)

(52) U.S. Cl.
CPC ............ *B62D 1/046* (2013.01); *A61B 5/6893* (2013.01); *B60R 16/027* (2013.01); *B62D 1/06* (2013.01); *B62D 1/08* (2013.01); *B62D 1/10* (2013.01); *A61B 5/02405* (2013.01); *A61B 5/165* (2013.01); *A61B 5/18* (2013.01); *A61B 2562/166* (2013.01)

(58) Field of Classification Search
CPC ....................................................... B62D 1/08
See application file for complete search history.

(56) References Cited

U.S. PATENT DOCUMENTS

| | | | | |
|---|---|---|---|---|
| 6,104,296 A | * | 8/2000 | Yasushi ................. | A61B 5/222 340/576 |
| 9,820,685 B2 | * | 11/2017 | Rake ....................... | A61B 5/18 |
| 2017/0273630 A1 | * | 9/2017 | Seo ........................ | B60K 28/02 |

(Continued)

*Primary Examiner* — Vicky A Johnson
(74) *Attorney, Agent, or Firm* — Morgan, Lewis & Bockius LLP

(57) ABSTRACT

A steering wheel includes: a hub; a rim connected to the hub through a plurality of spokes; and a first steering wheel remote control and a second steering wheel remote control arranged on sides of the hub, respectively, in a symmetric manner. A biological parameter measuring apparatus includes: a first conductive bezel arranged around the first steering wheel remote control; a second conductive bezel arranged around the second steering wheel remote control; and a signal processor, which is electrically connected to the first and second conductive bezels, configured to process and calculate a biological parameter based on a signal detected by at least one of the first conductive bezel or the second conductive bezels. The first conductive bezel is spaced apart from the second conductive bezel.

18 Claims, 19 Drawing Sheets

(51) Int. Cl.
  *A61B 5/16* (2006.01)
  *A61B 5/18* (2006.01)

(56) References Cited

U.S. PATENT DOCUMENTS

2019/0077311 A1\* 3/2019 Ali .......................... B60Q 3/70
2019/0202383 A1\* 7/2019 Odate ..................... B62D 1/06

\* cited by examiner

STEERING WHEEL FOR MEASURING DRIVER BIOLOGICAL PARAMETER

CROSS-REFERENCE TO RELATED APPLICATION

This application is based on and claims the benefit of priority to Korean Patent Application No. 10-2020-0100749, filed on Aug. 11, 2020, in the Korean Intellectual Property Office, the disclosure of which is incorporated herein in its entirety by reference.

TECHNICAL FIELD

The present disclosure relates to a steering wheel, and more particularly, to a steering wheel capable of accurately measuring the driver's biological parameters.

BACKGROUND

A healthcare system for a vehicle, capable of monitoring the driver's biological parameters, health status, etc. to thereby manage the driver's health or prevent traffic accidents, is being developed. The vehicle healthcare system has various healthcare sensors (a heart rate sensor, an electrocardiogram sensor, etc.) to measure the driver's heart rate, electrocardiogram parameter, etc. The healthcare sensors may be mounted on a steering wheel, a seat, a cockpit module, and the like.

In an exemplary healthcare system, the healthcare sensors (a heart rate sensor, an electrocardiogram sensor, etc.) are mounted on a rim portion of the steering wheel. When the driver's hands hold the steering wheel, the healthcare sensors measure the driver's heart rate, heart rate variability, stress, etc. and transmit the measured results to a vehicle controller.

However, as the expensive healthcare sensors are mounted on the rim portion of the steering wheel, interference with other components such as heat rays may occur. In addition, the whole structure of the steering wheel needs to be changed and the overall assembly process is complicated, resulting in increased manufacturing cost.

The above information described in this background section is provided to assist in understanding the background of the inventive concept, and may include any technical concept which is not considered as the prior art that is already known to those skilled in the art.

SUMMARY

The present disclosure has been made to solve the above-mentioned problems occurring in the prior art while advantages achieved by the prior art are maintained intact.

An aspect of the present disclosure provides a steering wheel in which a biological parameter measuring apparatus including a pair of conductive bezels and a signal processor for measuring the driver's biological parameters is connected to steering wheel remote controls, thereby simplifying an assembly process and reducing manufacturing cost.

According to an aspect of the present disclosure, a steering wheel may include: a hub; a rim connected to the hub through a plurality of spokes; a first steering wheel remote control and a second steering wheel remote control symmetrically arranged on sides of the hub, respectively, in a symmetric manner; and a biological parameter measuring apparatus including: a first conductive bezel arranged around the first steering wheel remote control, a second conductive bezel arranged around the second steering wheel remote control, and a signal processor, which is electrically connected to the first and second conductive bezels, configured to process and calculate a biological parameter based on a signal detected by at least one of the first conductive bezel or the second conductive bezels. The first conductive bezel may be spaced apart from the second conductive bezel.

The signal processor may be electrically connected to a first printed circuit board (PCB) of the first steering wheel remote control, the first conductive bezel may be electrically connected to the signal processor, and the second conductive bezel may be electrically connected to a second PCB of the second steering wheel remote control.

The signal processor may have a processor-side connector, and the first PCB may have a board-side connector. As the processor-side connector and the board-side connector are joined, the signal processor may be electrically connected to the first PCB.

The first conductive bezel may have a first contact projection electrically connected to a contact of the signal processor.

The first contact projection may be electrically connected to the contact of the signal processor through a first bridge terminal.

The first contact projection may directly contact the contact of the signal processor.

The second conductive bezel may have a second contact projection electrically connected to a contact of the second PCB.

The second contact projection may be electrically connected to the contact of the second PCB through a second bridge terminal.

The second contact projection may directly contact the contact of the second PCB.

The signal processor may be integrally attached to the first PCB.

The steering wheel may further include: an armature providing a structural foundation for the hub, the plurality of spokes, and the rim; and a bottom member disposed under the armature. The first and second conductive bezels may be attached to a top surface of the armature, and the bottom member may be attached to a bottom surface of the armature. The first and second conductive bezels may be joined to the armature together with the bottom member through a plurality of screws, and the bottom member may be made of an insulating material.

The steering wheel may further include a cylindrical member detachably coupled to each of the first and second conductive bezels. The cylindrical member may be made of an insulating material, the cylindrical member may be interposed between each conductive bezel and the armature, and each screw may be screwed into the cylindrical member.

The armature may have a through-hole through which each screw passes, the bottom member may have a through-hole through which the screw passes, and the through-hole of the armature and the through-hole of the bottom member may have a diameter greater than that of the screw.

The cylindrical member may have a pair of first coupling protrusions spaced apart from each other by a predetermined gap, and each conductive bezel may have an insertion protrusion inserted into the gap between the pair of first coupling protrusions.

Each conductive bezel may have a pair of support walls spaced apart from each other, the pair of support walls may be spaced apart from each other by a gap corresponding to a diameter of the cylindrical member, each support wall may have a coupling hole, the cylindrical member may have a pair of second coupling protrusions opposing each other, the pair of second coupling protrusions may protrude from an exterior surface of the cylindrical member in a manner that the pair of second coupling protrusions may be perpendicular to the pair of first coupling protrusions, and each second coupling protrusion may be inserted into the coupling hole of the corresponding support wall.

Each conductive bezel may have a cylindrical portion protruding toward the armature, the cylindrical portion may pass through a through-hole of the armature, and each screw may pass through the bottom member and be screwed into the cylindrical portion.

An insulating layer may be attached to an exterior surface of the cylindrical portion.

BRIEF DESCRIPTION OF THE DRAWINGS

The above and other objects, features and advantages of the present disclosure will be more apparent from the following detailed description taken in conjunction with the accompanying drawings.

DETAILED DESCRIPTION

Figure 1:
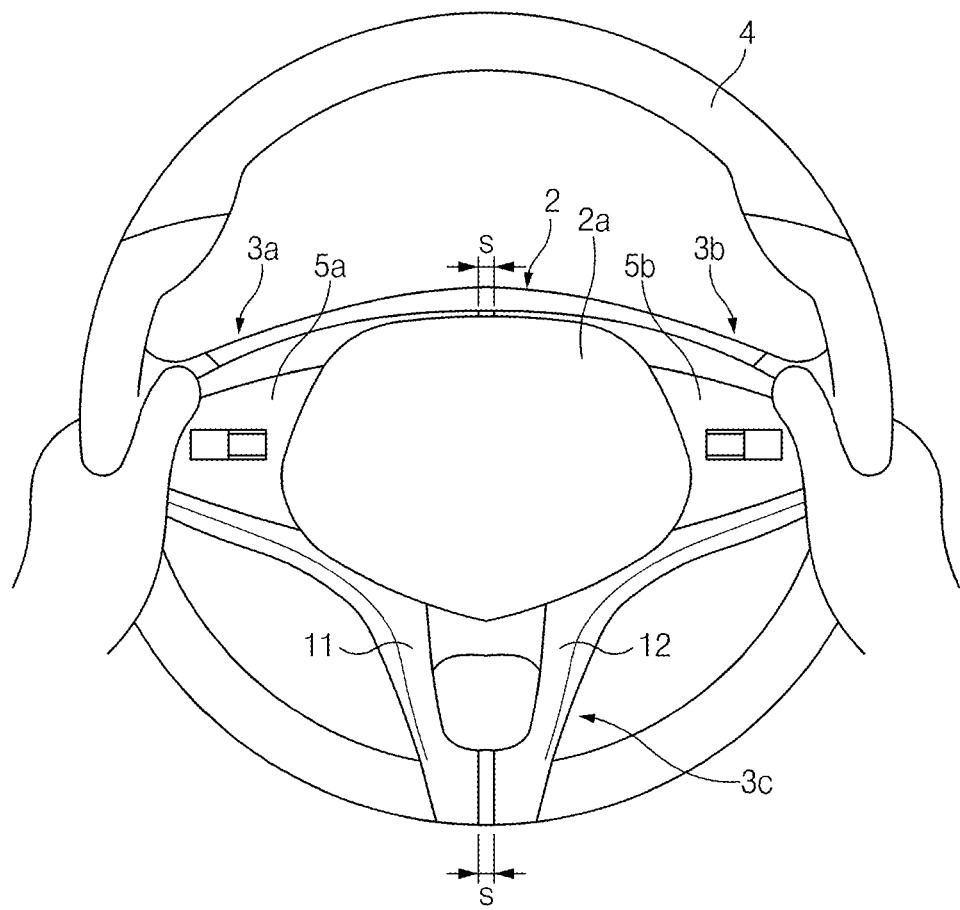
FIG. 1 illustrates a plan view of a steering wheel according to an exemplary embodiment of the present disclosure.

Hereinafter, exemplary embodiments of the present disclosure will be described in detail with reference to the accompanying drawings. In the drawings, the same reference numerals will be used throughout to designate the same or equivalent elements. In addition, a detailed description of well-known techniques associated with the present disclosure will be ruled out in order not to unnecessarily obscure the gist of the present disclosure.

Terms such as first, second, A, B, (a), and (b) may be used to describe the elements in exemplary embodiments of the present disclosure. These terms are only used to distinguish one element from another element, and the intrinsic features, sequence or order, and the like of the corresponding elements are not limited by the terms. Unless otherwise defined, all terms used herein, including technical or scientific terms, have the same meanings as those generally understood by those with ordinary knowledge in the field of art to which the present disclosure belongs. Such terms as those defined in a generally used dictionary are to be interpreted as having meanings equal to the contextual meanings in the relevant field of art, and are not to be interpreted as having ideal or excessively formal meanings unless clearly defined as having such in the present application.

Referring to FIG. 1, a steering wheel 1 may include a hub 2, a plurality of spokes 3a, 3b, and 3c extending radially from the hub 2, a rim 4 connected to the hub 2 through the plurality of spokes 3a, 3b, and 3c, and a biological parameter measuring apparatus 10 disposed on the plurality of spokes 3a, 3b, and 3c.

The hub 2 may be located in the middle of the steering wheel 1, and a driver airbag (DBA) 2a may be disposed in the hub 2. FIG. 1 illustrates first and second spokes 3a and 3b symmetrically disposed on the left and right sides of the hub 2 and a third spoke 3c located between the first spoke 3a and the second spoke 3b. The rim 4 may have an annular shape extending along a circumferential direction.

A plurality of steering wheel remote controls 5a and 5b (also called "steering control interface") may be mounted on some spokes 3a and 3b of the plurality of spokes 3a, 3b, and 3c, respectively. For example, the pair of steering wheel remote controls 5a and 5b may be mounted on the pair of spokes 3a and 3b disposed on the left and right sides of the steering wheel 1, respectively. The steering wheel remote controls 5a and 5b may control functions of various parts/components equipped in the vehicle, such as an audio device, a hands-free device, a gearshift, a cruise control, an air conditioner, a lighting device, a wiper, a navigation device, an instrument cluster, and an audio video navigation (AVN) system. Each of the steering wheel remote controls 5a and 5b may indirectly control the vehicle components through a vehicle controller, or may directly control the vehicle components.

Figure 2:
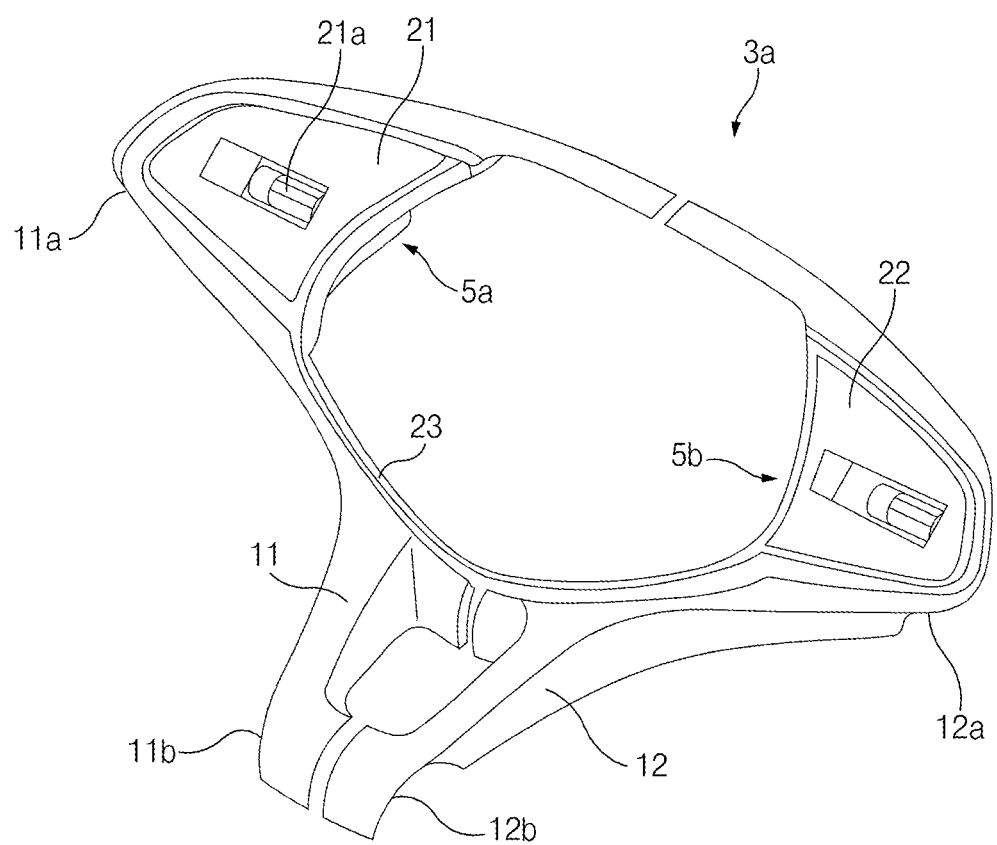
FIG. 2 illustrates a top perspective view of first and second steering wheel remote controls and first and second conductive bezels in a steering wheel according to an exemplary embodiment of the present disclosure.
Figure 3:
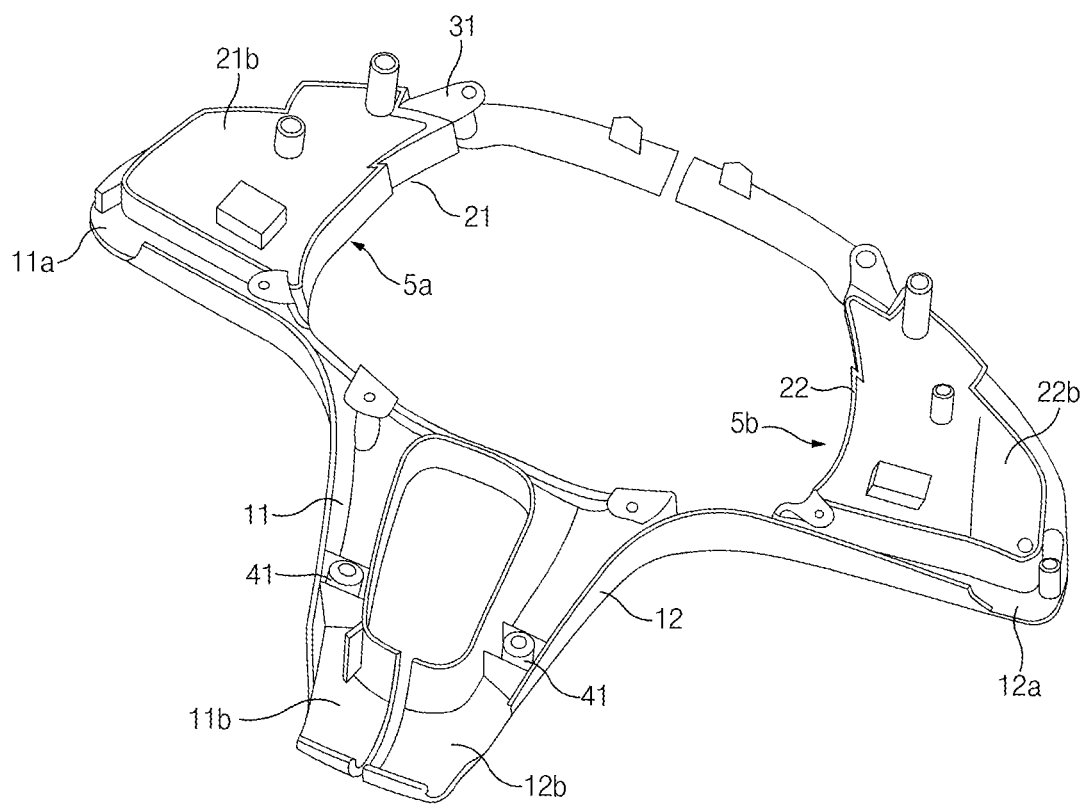
FIG. 3 illustrates a bottom perspective view of first and second steering wheel remote controls and first and second conductive bezels in a steering wheel according to an exemplary embodiment of the present disclosure.

Referring to FIGS. 2 and 3, the pair of steering wheel remote controls 5a and 5b may include a first steering wheel remote control 5a located on the first spoke 3a and a second steering wheel remote control 5b located on the second spoke 3b. The first steering wheel remote control 5a and the second steering wheel remote control 5b may be symmetrically arranged on both sides of the hub 2.

The first steering wheel remote control 5a may include a first housing 21, and the first housing 21 may have a first input unit 21a disposed on a top surface thereof and a bottom opening defined in a bottom end thereof. A first lower cover 21b may be mounted on the first housing 21 to cover the bottom opening of the first housing 21. The second steering wheel remote control 5b may include a second housing 22, and the second housing 22 may have a second input unit 22a disposed on a top surface thereof and a bottom opening defined in a bottom end thereof. A second lower cover 22b may be mounted on the second housing 22 to cover the bottom opening of the second housing 22.

Figure 4:
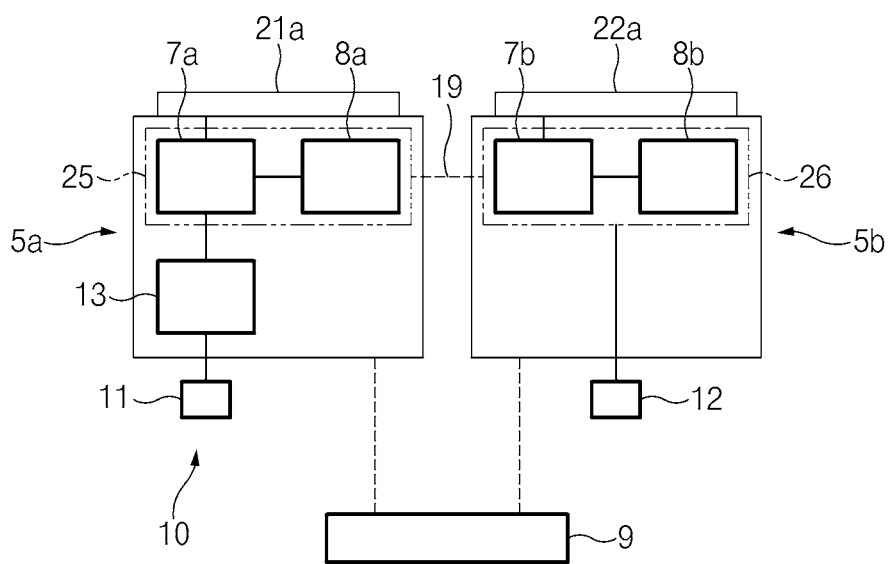
FIG. 4 illustrates a block diagram of a control configuration of a steering wheel according to an exemplary embodiment of the present disclosure.
Figure 5:
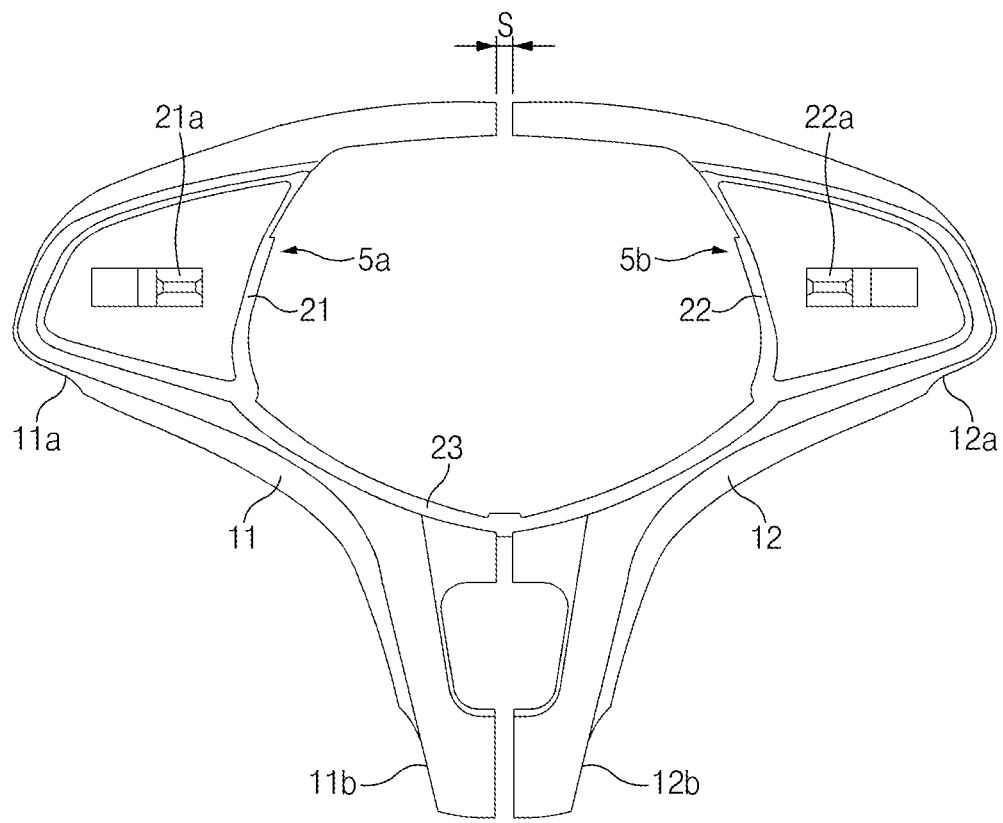
FIG. 5 illustrates a plan view of first and second steering wheel remote controls and first and second conductive bezels in a steering wheel according to an exemplary embodiment of the present disclosure.

Referring to FIG. 4, the first steering wheel remote control 5a may include a first processor 7a processing a signal input to the first input unit 21a and transmitting the processed signal to a vehicle controller 9 such as a body control module (BCM) or to each individual component, and a first memory 8a storing software for executing signal processing, control functions, etc. The second steering wheel remote control 5b may include a second processor 7b processing a signal input to the second input unit 22a and transmitting the processed signal to the vehicle controller 9 such as the BCM or to each individual component, and a second memory 8b storing software for executing signal processing, control functions, etc.

Figure 7:
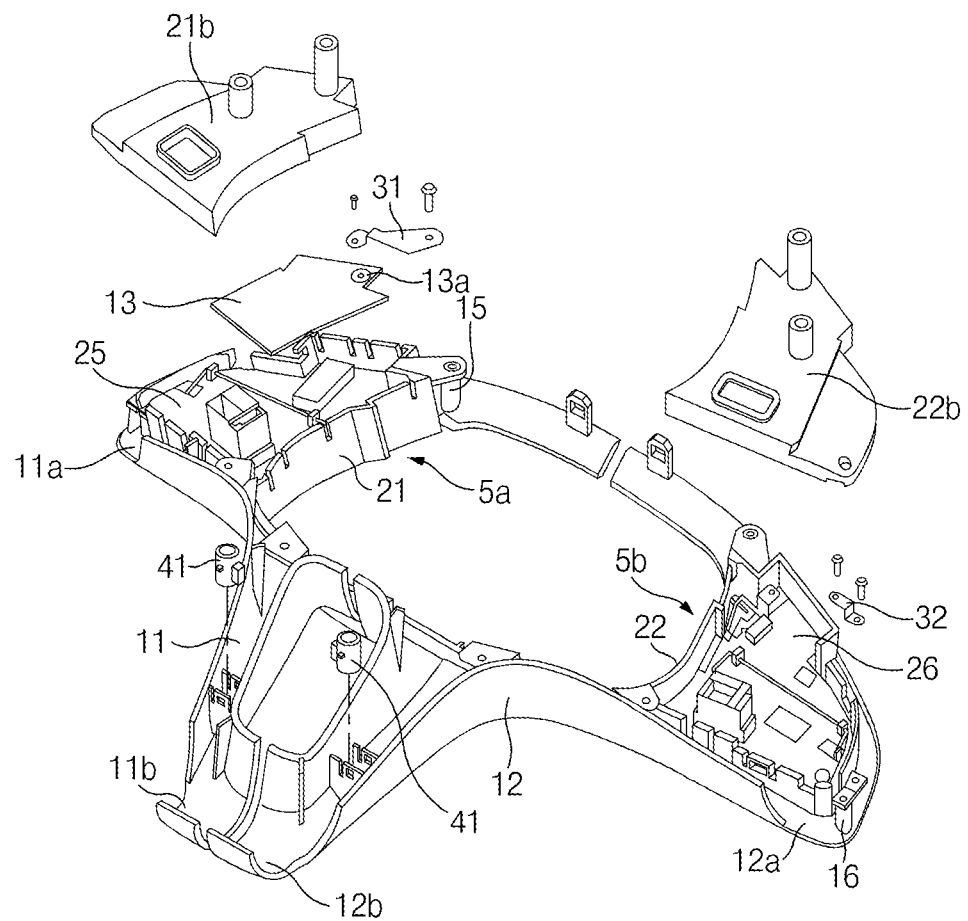
FIG. 7 illustrates an exploded perspective view of first and second steering wheel remote controls in a steering wheel according to an exemplary embodiment of the present disclosure.

Referring to FIGS. 4 and 7, a first printed circuit board (PCB) 25 may be disposed within the first housing 21 of the first steering wheel remote control 5a, and the first processor 7a and the first memory 8a may be provided on the first PCB 25. A second PCB 26 may be disposed within the second housing 22 of the second steering wheel remote control 5b, and the second processor 7b and the second memory 8b may be provided on the second PCB 26. Referring to FIG. 4, a conductive pattern of the first PCB 25 may be electrically connected to a conductive pattern of the second PCB 26 through an electric wire 19. The electric wire 19 may be a shielded electric wire.

The biological parameter measuring apparatus 10 may measure biological parameters such as a stress index and electrocardiogram parameters including a heart rate and heart rate variability.

According to an exemplary embodiment, the biological parameter measuring apparatus 10 may include a pair of conductive bezels 11 and 12 spaced apart from each other, and a signal processor 13 calculating the biological parameters based on signals detected by at least one of the pair of conductive bezels 11 and 12.

Referring to FIGS. 1 to 3, the pair of conductive bezels 11 and 12 may have a shape corresponding to that of the spokes 3a, 3b, and 3c of the steering wheel 1. The pair of conductive bezels 11 and 12 may include a first conductive bezel 11 disposed around the first steering wheel remote control 5a, and a second conductive bezel 12 disposed around the second steering wheel remote control 5b.

The first conductive bezel 11 and the second conductive bezel 12 may be made of a material having electrical conductivity. For example, the first conductive bezel 11 and the second conductive bezel 12 may be made of a material in which a resin surface is coated with a conductive metal layer such as chrome. Alternatively, the first conductive bezel 11 and the second conductive bezel 12 may be made of a conductive metal material. The first conductive bezel 11 and the second conductive bezel 12 may be spaced apart from each other by a predetermined gap s. That is, the first conductive bezel 11 may be a first electrode, and the second conductive bezel 12 may be a second electrode. When the driver's left and right hands touch the first conductive bezel 11 and the second conductive bezel 12, a potential difference (voltage) between the first conductive bezel 11 and the second conductive bezel 12 may be created with respect to a reference potential such as the ground.

The first conductive bezel 11 may have two fitting portions 11a and 11b fitted into the rim 4 of the steering wheel 1. One fitting portion 11a may be adjacent to the first housing 21 of the first steering wheel remote control 5a, and the other fitting portion 11b may be relatively far away from the first housing 21 of the first steering wheel remote control 5a. The second conductive bezel 12 may have two fitting portions 12a and 12b fitted into the rim 4 of the steering wheel 1. One fitting portion 12a may be adjacent to the second housing 22 of the second steering wheel remote control 5b, and the other fitting portion 12b may be relatively far away from the second housing 22 of the second steering wheel remote control 5b. That is, the first conductive bezel 11 and the second conductive bezel 12 may form top portions of the spokes 3a, 3b, and 3c of the steering wheel 1.

The first conductive bezel 11 and the second conductive bezel 12 may be electrically connected to the signal processor 13. The signal processor 13 may calculate the biological parameters by differentially amplifying and analyzing electrical signals (potential difference) output from the pair of conductive bezels 11 and 12, and transmit the calculated biological parameters to the vehicle controller 9 such as the BCM. For example, the biological parameters may include electrocardiogram parameters such as a heart rate and heart rate variability, and a stress index.

According to an exemplary embodiment, the signal processor 13 may be a hardware module independent of the first PCB 25 of the first steering wheel remote control 5a or the second PCB 26 of the second steering wheel remote control 5b. The signal processor 13 may be electrically connected to any one of the first steering wheel remote control 5a and the second steering wheel remote control 5b.

In the present disclosure, the signal processor 13 may be a microprocessor chip also known as a digital signal processor (DSP) used in audio signal processing, telecommunications, digital image processing, radar, sonar, and speech recognition systems, and in common consumer electronic devices.

Referring to FIGS. 4, 7, 8, and 9, the signal processor 13 may be electrically connected to the first steering wheel remote control 5a, and the first conductive bezel 11 may be electrically connected to the signal processor 13. The signal processor 13 may be electrically connected to the first PCB 25 of the first steering wheel remote control 5a, and the second conductive bezel 12 may be electrically connected to the second PCB 26 of the second steering wheel remote control 5b. Referring to FIG. 4, the first PCB 25 of the first steering wheel remote control 5a may be electrically connected to the second PCB 26 of the second steering wheel remote control 5b through the electric wire 19. Thus, the first conductive bezel 11 and the second conductive bezel 12 may be electrically connected to the signal processor 13.

Figure 8:
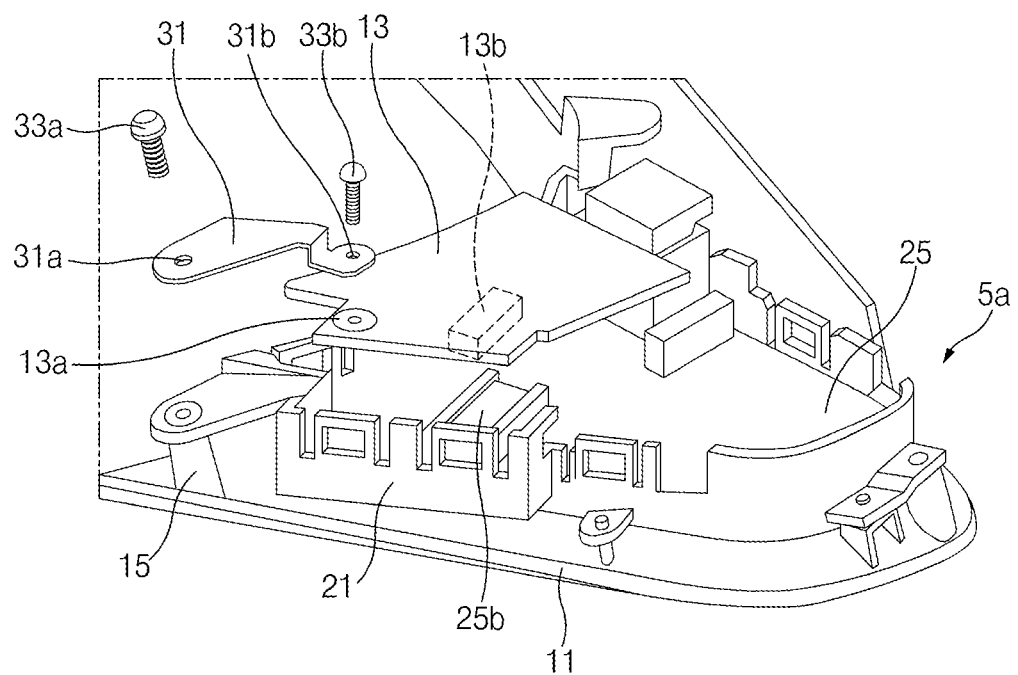
FIG. 8 illustrates an exploded perspective view of a first steering wheel remote control in a steering wheel according to an exemplary embodiment of the present disclosure.

Referring to FIG. 8, the signal processor 13 may have a processor-side connector 13b, and the first PCB 25 may have a board-side connector 25b. The processor-side connector 13b has a shape to be fitted in the board-side connector 25b, such that when the processor-side connector 13b is disposed in the board-side connector 25b, the signal processor 13 may be electrically connected to the first PCB 25.

According to another exemplary embodiment, the signal processor 13 may be a hardware module integrally attached to the first PCB 25 of the first steering wheel remote control 5a.

According to another exemplary embodiment, the signal processor 13 may be a software module (for example, a processing program) stored in the first memory 8a of the first steering wheel remote control 5a or the second memory 8b of the second steering wheel remote control 5b.

Figure 6:
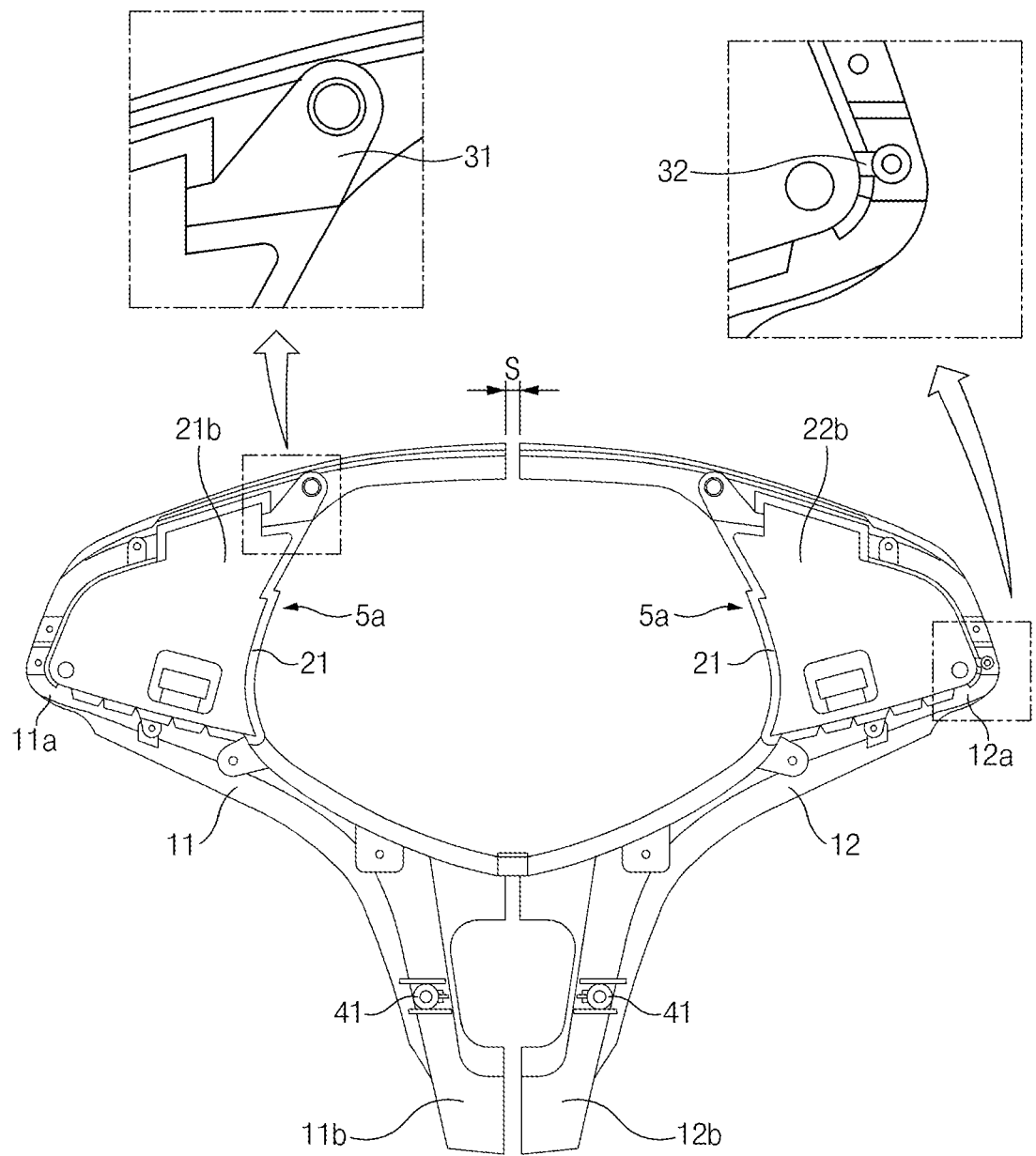
FIG. 6 illustrates a bottom view of first and second steering wheel remote controls and first and second conductive bezels in a steering wheel according to an exemplary embodiment of the present disclosure.

Referring to FIGS. 6, 7, and 8, the first conductive bezel 11 may be electrically connected to the signal processor 13 through a first bridge terminal 31. The first conductive bezel 11 may have a first contact projection 15, and the first contact projection 15 may have a shape extending or protruding from an edge of the first conductive bezel 11. The first contact projection 15 may be spaced apart from the signal processor 13 and the first PCB 25. The signal processor 13 may have a first contact 13a having a disk shape, and the first bridge terminal 31 may have a first bezel-side through-hole 31a and a processor-side through-hole 31b. The first bezel-side through-hole 31a may be defined to be aligned with the first contact projection 15, and the processor-side through-hole 31b may be defined to be aligned with a through-hole of the contact 13a. A first bezel-side screw 33a may pass through the first bezel-side through-hole 31a of the first bridge terminal 31 and be screwed to the first contact projection 15, and a processor-side screw 33b may pass through the processor-side through-hole 31b of the first bridge terminal 31 and the through-hole of the contact 13a and be screwed to the first PCB 25 so that the first bridge terminal 31 may be electrically connected to the first conductive bezel 11 and the contact 13a of the signal processor 13. For example, the first bridge terminal 31 may be integrally formed with the first housing 21 by insert injection molding.

Figure 9:
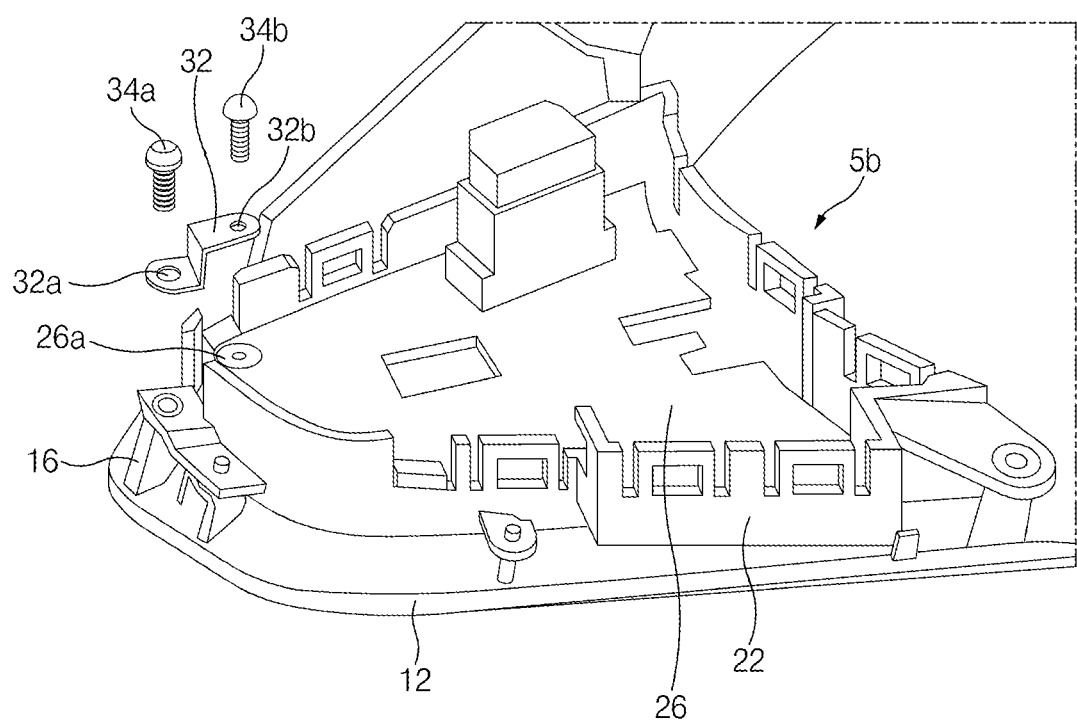
FIG. 9 illustrates an exploded perspective view of a second steering wheel remote control in a steering wheel according to an exemplary embodiment of the present disclosure.

Referring to FIGS. 6, 7, and 9, the second conductive bezel 12 may be electrically connected to the second PCB 26 through a second bridge terminal 32. The second conductive bezel 12 may have a second contact projection 16, and the second contact projection 16 may have a shape extending or protruding from an edge of the second conductive bezel 12. The second contact projection 16 may be spaced apart from the second PCB 26. The second PCB 26 may have a contact 26a having a disk shape, and the second bridge terminal 32 may have a second bezel-side through-hole 32a and a board-side through-hole 32b. The second bezel-side through-hole 32a may be defined to be aligned with the second contact projection 16, and the board-side through-hole 32b may be defined to be aligned with a through-hole of the contact 26a. A second bezel-side screw 34a may pass through the second bezel-side through-hole 32a of the second bridge terminal 32 and be screwed to the second contact projection 16, and a board-side screw 34b may pass through the board-side through-hole 32b of the second bridge terminal 32 and the through-hole of the contact 26a and be screwed to the second PCB 26 so that the second bridge terminal 32 may be electrically connected to the second conductive bezel 12 and the second PCB 26. For example, the second bridge terminal 32 may be integrally formed with the second housing 22 by insert injection molding.

Figure 10:
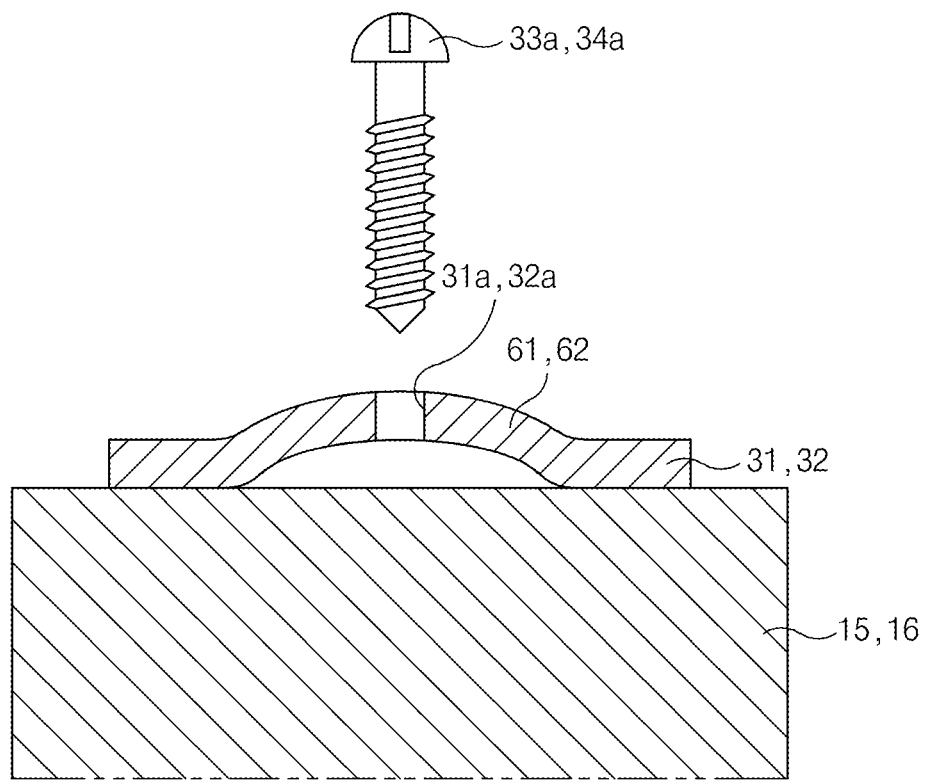
FIG. 10 illustrates first and second dome portions of first and second bridge terminals in a steering wheel according to an exemplary embodiment of the present disclosure.
Figure 11:
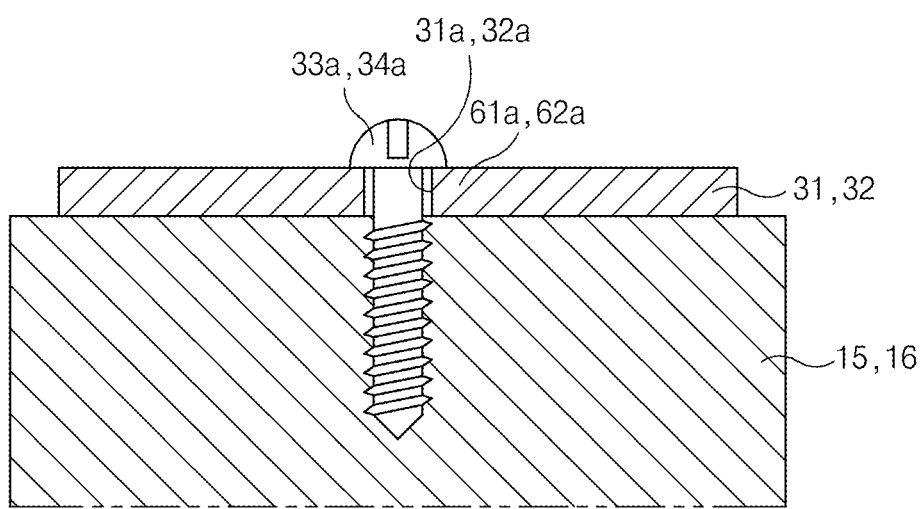
FIG. 11 illustrates a state in which the first and second bridge terminals illustrated in FIG. 10 are screwed to first and second contact projections.

Referring to FIG. 10, the first bridge terminal 31 may have a first dome portion 61 provided around the first bezel-side through-hole 31a, and the first dome portion 61 may be convex upwardly from the first bridge terminal 31. Referring to FIG. 11, when the first bezel-side screw 33a passes through the first bezel-side through-hole 31a and is screwed to the first contact projection 15, a head portion of the first bezel-side screw 33a may press the first dome portion 61 to a top surface of the first contact projection 15 so that the first dome portion 61 may be transformed into a flat portion 61a. As a bottom surface of the first dome portion 61 tightly contacts the top surface of the first contact projection 15, a contact area between the first bridge terminal 31 and the first contact projection 15 of the first conductive bezel 11 may relatively increase, thereby ensuring electrical contact safety and high signal quality between the first conductive bezel 11 and the first bridge terminal 31.

Referring to FIG. 10, the second bridge terminal 32 may have a second dome portion 62 provided around the second bezel-side through-hole 32a, and the second dome portion 62 may be convex upwardly from the second bridge terminal 32. Referring to FIG. 11, when the second bezel-side screw 34a passes through the second bezel-side through-hole 32a and is screwed to the second contact projection 16, a head portion of the second bezel-side screw 34a may press the second dome portion 62 to a top surface of the second contact projection 16 so that the second dome portion 62 may be transformed into a flat portion 62a. As a bottom surface of the second dome portion 62 tightly contacts the top surface of the second contact projection 16, a contact area between the second bridge terminal 32 and the second contact projection 16 of the second conductive bezel 12 may relatively increase, thereby ensuring electrical contact safety and high signal quality between the second conductive bezel 12 and the second bridge terminal 32.

Figure 12:
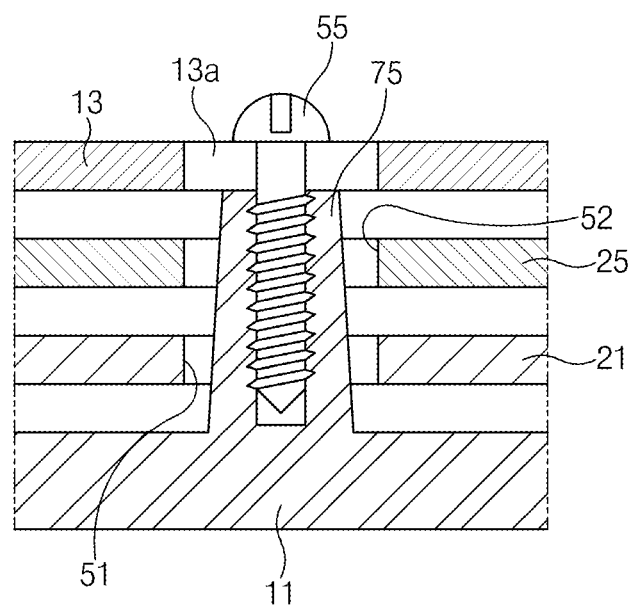
FIG. 12 illustrates a state in which a first contact projection of a first conductive bezel contacts a contact of a signal processor in a steering wheel according to an exemplary embodiment of the present disclosure.

According to another exemplary embodiment, a first contact projection 75 may be directly connected to the signal processor 13 without the first bridge terminal 31. Referring to FIG. 12, the first contact projection 75 may pass through the first housing 21 and the first PCB 25. The first contact projection 75 may protrude from the first conductive bezel 11 toward the signal processor 13, and the first contact projection 75 may directly contact the contact 13a of the signal processor 13. As a first bezel-side screw 55 passes through the through-hole of the contact 13a and is screwed to the first contact projection 75, the first contact projection 75 may be electrically connected to the contact 13a of the signal processor 13 without the first bridge terminal 31. The first housing 21 may have a through-hole 51 through which the first contact projection 75 passes, and the first PCB 25 may have a through-hole 52 through which the first contact projection 75 passes. As the first contact projection 75 passes through the through-hole 51 of the first housing 21 and the through-hole 52 of the first PCB 25, a top surface of the first contact projection 75 may directly contact a bottom surface of the contact 13a of the signal processor 13.

Figure 13:
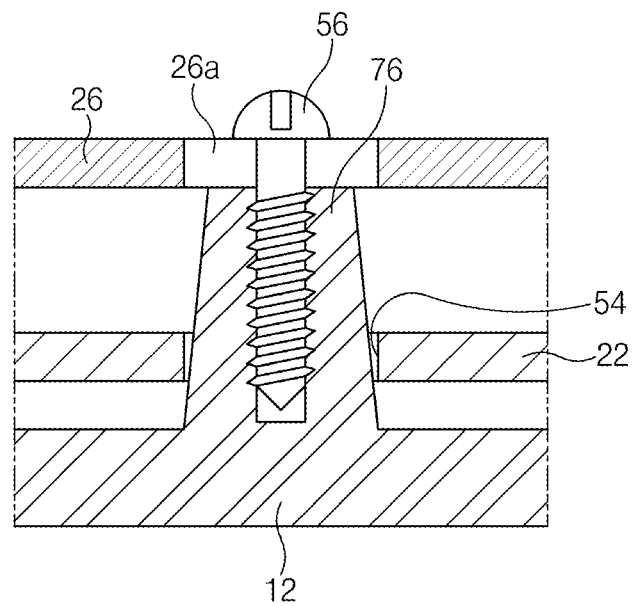
FIG. 13 illustrates a state in which a second contact projection of a second conductive bezel contacts a contact of a second printed circuit board (PCB) in a steering wheel according to an exemplary embodiment of the present disclosure.

According to another exemplary embodiment, a second contact projection 76 may be directly connected to the second PCB 26 without the second bridge terminal 32. Referring to FIG. 13, the second contact projection 76 may pass through the second housing 22. The second contact projection 76 may protrude from the second conductive bezel 12, and the second contact projection 76 may directly contact the contact 26a of the second PCB 26. As a second bezel-side screw 56 passes through the through-hole of the contact 26a and is screwed to the second contact projection 76, the second contact projection 76 may be electrically connected to the contact 26a of the second PCB 26 without the second bridge terminal 32. The second housing 22 may have a through-hole 54 through which the second contact projection 76 passes. As the second contact projection 76 passes through the through-hole 54 of the second housing 22, a top surface of the second contact projection 76 may directly contact a bottom surface of the contact 26a of the second PCB 26.

Figure 14:
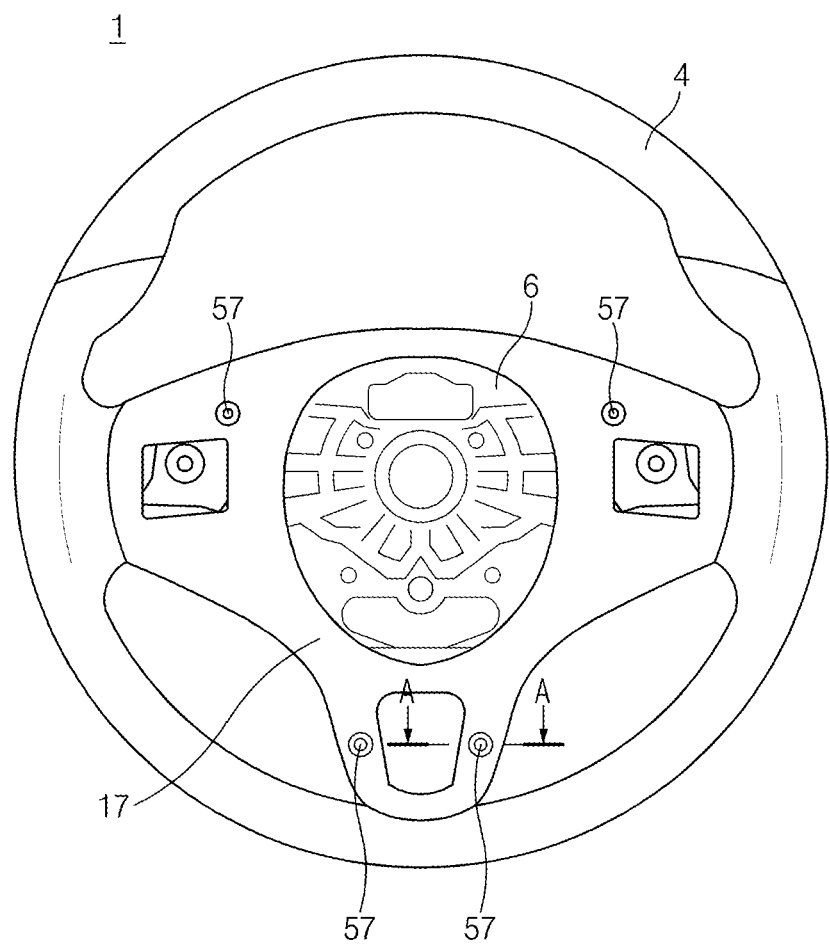
FIG. 14 illustrates a bottom view of a steering wheel according to an exemplary embodiment of the present disclosure.

Referring to FIG. 14, the steering wheel 1 according to an exemplary embodiment of the present disclosure may further include an armature 6 providing a structural foundation of the steering wheel, and a bottom member 17 arranged or disposed under the armature 6.

The armature 6 may be made of a metal material such as an aluminum alloy and a magnesium alloy. In particular, the armature 6 may provide a basic framework for the rim 4, the hub 2, and the plurality of spokes 3a, 3b, and 3c. The hub 2, the plurality of spokes 3a, 3b, 3c, and the rim 4 are connected to the armature 6 as a center of the steering wheel.

Figure 15:
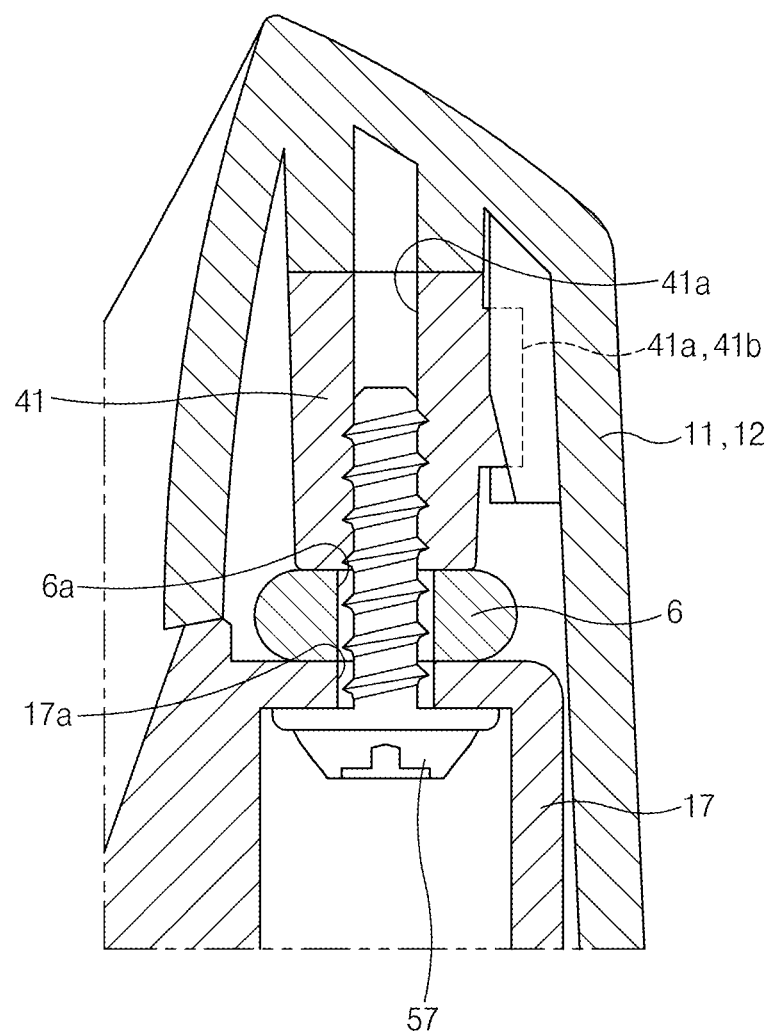
FIG. 15 illustrates a cross-sectional view, taken along line A-A of FIG. 14.

Referring to FIG. 15, as the first and second conductive bezels 11 and 12 are attached to a top surface of the armature 6, the first and second conductive bezels 11 and 12 may become the top portions of the spokes 3a, 3b, and 3c, and as the bottom member 17 is attached to a bottom surface of the armature 6, the bottom member 17 may become bottom portions of the spokes 3a, 3b, and 3c. The first and second conductive bezels 11 and 12 may be connected to the armature 6 together with the bottom member 17 through a plurality of screws 57. The armature 6 may have through-holes 6a, each of which has a larger diameter than an outer diameter of the screw 57. The bottom member 17 may have through-holes 17a, each of which has a larger diameter than the outer diameter of the screw 57. The bottom member 17 may be made of an insulating material such as resin.

Referring to FIG. 15, at least one cylindrical member 41 may be detachably coupled to each of the conductive bezels 11 and 12. The cylindrical member 41 may be made of an insulating material such as resin, and the cylindrical member 41 may be located on the armature 6. In particular, the cylindrical member 41 may be interposed between the conductive bezels 11 and 12 and the armature 6. As each screw 57 passes through the through-hole 17a of the bottom member 17 and the through-hole 6a of the armature 6 and is screwed into an inner hole 41a of the cylindrical member 41, each of the conductive bezels 11 and 12 may be joined to the armature 6 together with the bottom member 17. The diameter of the through-hole 6a of the armature 6 and the diameter of the through-hole 17a of the bottom member 17 may be greater than the diameter of the screw 57, and the screw 57 may be screwed into the cylindrical member 41 of the insulating material, and thus electrical connection between the conductive bezels 11 and 12 and the armature 6 may be blocked.

Figure 16:
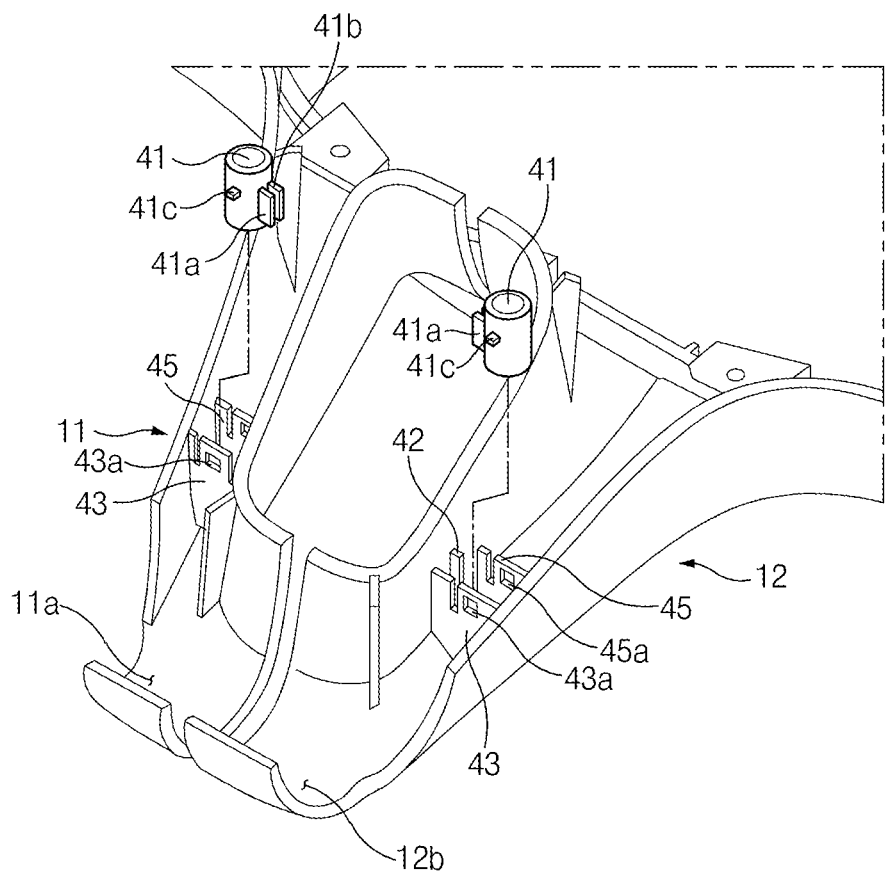
FIG. 16 illustrates an exploded perspective view of a state in which cylindrical members are separated from conductive bezels, respectively, in a steering wheel according to an exemplary embodiment of the present disclosure.
Figure 17:
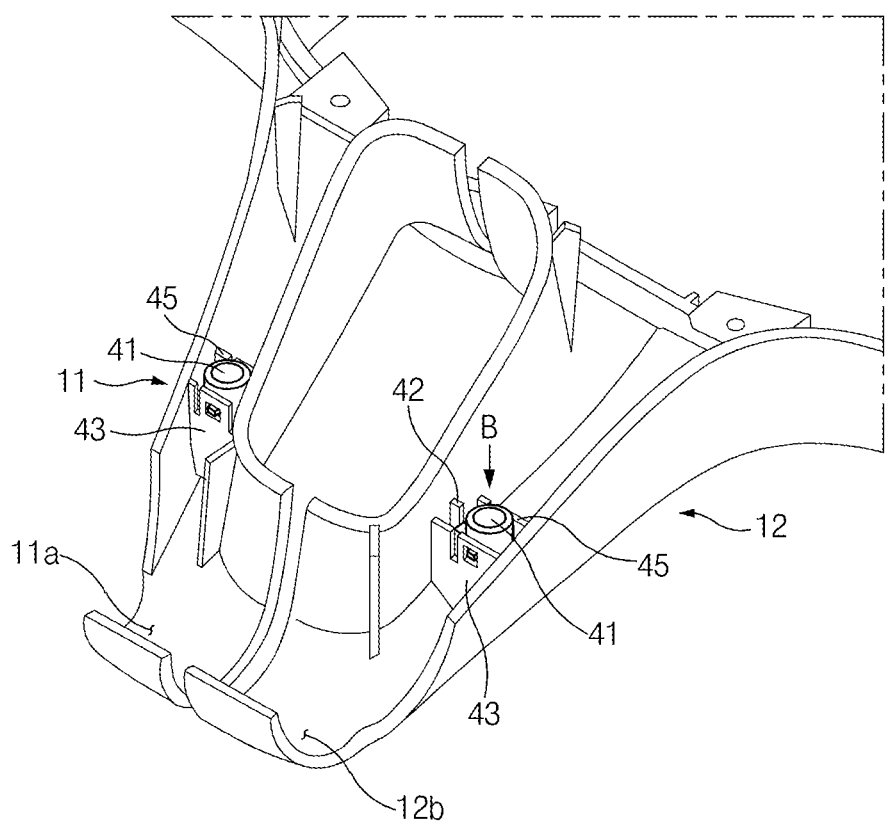
FIG. 17 illustrates a perspective view of a state in which the cylindrical members illustrated in FIG. 16 are coupled to the conductive bezels, respectively.
Figure 18:
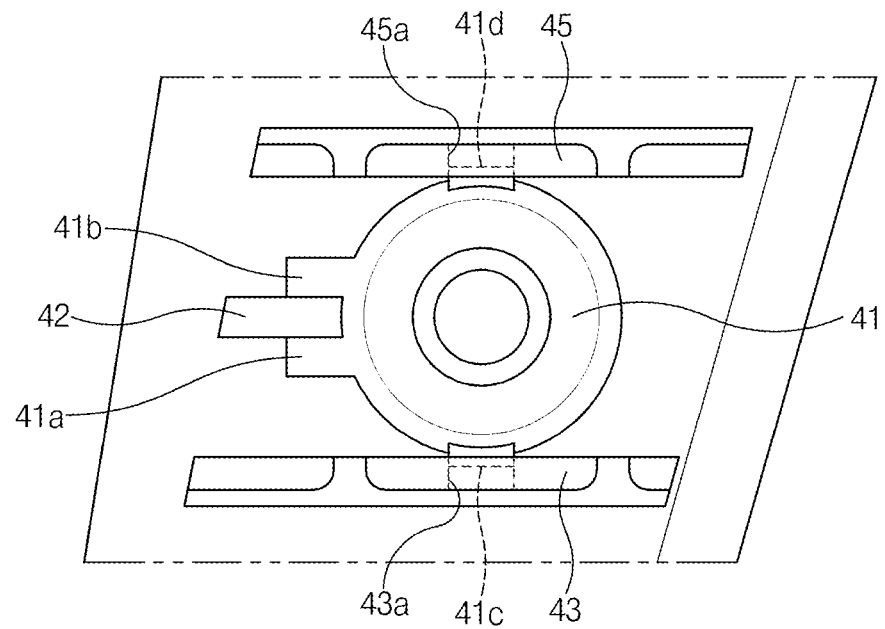
FIG. 18 illustrates a view which is viewed from a direction indicated by arrow B of FIG. 17.

Referring to FIGS. 16 to 18, the cylindrical members 41 may be detachably coupled to the conductive bezels 11 and 12, respectively. The cylindrical member 41 may have a pair of first coupling protrusions 41a and 41b spaced apart from each other, and the pair of first coupling protrusions 41a and 41b may protrude from an exterior surface of the cylindrical member 41. The pair of first coupling protrusions 41a and 41b may be parallel to each other. Each of the conductive bezels 11 and 12 may have an insertion protrusion 42, and the insertion protrusion 42 may be parallel to the pair of first coupling protrusions 41a and 41b. The insertion protrusion 42 of the conductive bezel may have a thickness corresponding to a gap between the pair of first coupling protrusions 41a and 41b, and thus the insertion protrusion 42 may be inserted into or extend through the gap between the pair of first coupling protrusions 41a and 41b.

Referring to FIGS. 16 to 18, each of the conductive bezels 11 and 12 may have a pair of support walls 43 and 45, and the pair of support walls 43 and 45 may be spaced apart from each other by a gap corresponding to a diameter of the cylindrical member 41. The pair of support walls 43 and 45 may be parallel to each other, and the support walls 43 and 45 may have coupling holes 43a and 45a, respectively. The cylindrical member 41 may have a pair of second coupling protrusions 41c and 41d opposing each other, and the pair of second coupling protrusions 41c and 41d may protrude from the exterior surface of the cylindrical member 41 in a manner that they are perpendicular to the pair of first coupling protrusions 41a and 41b. The second coupling protrusions 41c and 41d may be inserted into or extend through the coupling holes 43a and 45a of the corresponding support walls 43 and 45, respectively. The second coupling protrusions 41c and 41d may be spaced apart from the first coupling protrusions 41a and 41b at an angle of 90° on the exterior surface of the cylindrical member 41.

As the insertion protrusion 42 is inserted into or extend through the gap between the pair of first coupling protrusions 41a and 41b, and the second coupling protrusions 41c and 41d are inserted into or extend through the coupling holes 43a and 45a of the corresponding support walls 43 and 45, the cylindrical member 41 may be firmly mounted to each of the conductive bezels 11 and 12.

Figure 19:
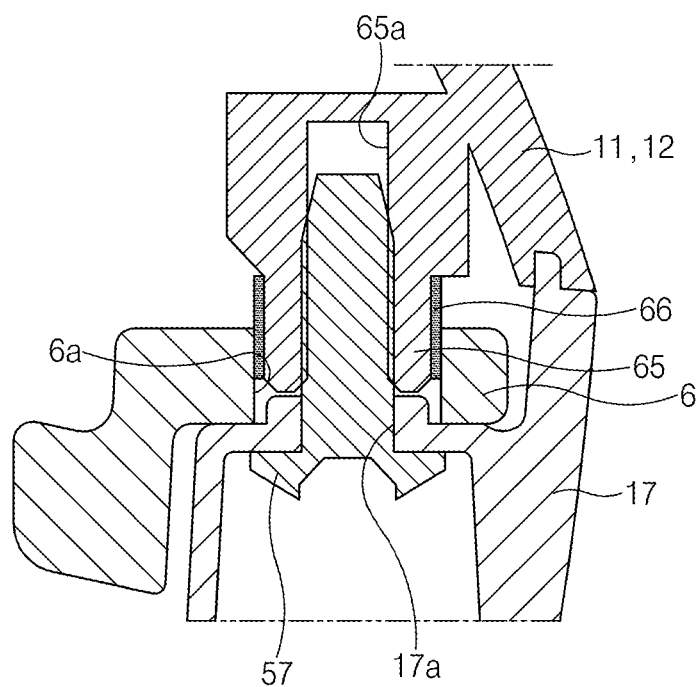
FIG. 19 illustrates a cross-sectional view of a state in which a cylindrical portion protruding from each conductive bezel is screwed to an armature together with a bottom member in a steering wheel according to another exemplary embodiment of the present disclosure.

According to another exemplary embodiment, as illustrated in FIG. 19, each of the conductive bezels 11 and 12 may have a cylindrical portion 65, and the cylindrical portion 65 may protrude from each of the conductive bezels 11 and 12 toward the armature 6 and the bottom member 17. The through-hole 6a of the armature 6 may have a larger diameter than a diameter of the cylindrical portion 65. The cylindrical portion 65 may pass through the through-hole 6a of the armature 6, and the screw 57 may pass through the through-hole 17a of the bottom member 17 and be screwed into an inner hole 65a of the cylindrical portion 65. An insulating layer 66 such as insulating tape may be attached to an exterior surface of the cylindrical portion 65, and thus electrical connection between the conductive bezels 11 and 12 and the armature 6 may be blocked.

As set forth above, according to exemplary embodiments of the present disclosure, the biological parameter measuring apparatus including the pair of conductive bezels and the signal processor for measuring the driver's biological parameters may be connected to the steering wheel remote controls, and thus the assembly process may be simplified and the manufacturing cost may be reduced.

According to exemplary embodiments of the present disclosure, the pair of conductive bezels may be disposed around the pair of steering wheel remote controls, respectively, and thus the driver's biological parameters may be easily and accurately measured.

According to exemplary embodiments of the present disclosure, the electrical connection between the first conductive bezel and the signal processor and the electrical connection between the second conductive bezel and the second PCB may be stably established.

Hereinabove, although the present disclosure has been described with reference to exemplary embodiments and the accompanying drawings, the present disclosure is not limited thereto, but may be variously modified and altered by those skilled in the art to which the present disclosure pertains without departing from the spirit and scope of the present disclosure claimed in the following claims.

What is claimed is:

1. A steering wheel, comprising:
    a hub;
    a rim connected to the hub through a plurality of spokes;
    a first steering wheel remote control and a second steering wheel remote control arranged on sides of the hub, respectively, in a symmetric manner; and
    a biological parameter measuring apparatus including:
        a first conductive bezel arranged around the first steering wheel remote control;
        a second conductive bezel arranged around the second steering wheel remote control; and
        a signal processor, which is electrically connected to the first and second conductive bezels, configured to process and calculate a biological parameter based on a signal detected by at least one of the first conductive bezel or the second conductive bezels,
    wherein the first conductive bezel is arranged to be spaced apart from the second conductive bezel,
    wherein the signal processor is electrically connected to a first printed circuit board (PCB) of the first steering wheel remote control,
    wherein the first conductive bezel is electrically connected to the signal processor,
    wherein the second conductive bezel is electrically connected to a second PCB of the second steering wheel remote control,
    wherein the signal processor has a processor-side connector,
    wherein the first PCB has a board-side connector, and
    wherein the processor-side connector has a shape to be fitted in the board-side connector, such that when the processor-side connector is disposed in the board-side connector, the signal processor is electrically connected to the first PCB.

2. The steering wheel according to claim 1, wherein the signal processor has a first contact having a disk shape,
    wherein the first conductive bezel has a first contact projection, which has a shape extending from an edge of the first conductive bezel and is spaced apart from the signal processor and the first PCB, electrically connected to the first contact.

3. The steering wheel according to claim 2, wherein the first contact projection is electrically connected to the first contact through a first bridge terminal.

4. The steering wheel according to claim 3, wherein the first bridge terminal comprises:
    a first bezel-side through-hole defined to be aligned with the first contact projection;
    a processor-side through-hole defined to be aligned with a through-hole of the first contact; and
    a first bezel-side screw configured to pass through the first bezel-side through-hole and the first contact projection; and
    a processor-side screw configured to pass through the processor-side through-hole and the through-hole of the first contact.

5. The steering wheel according to claim 4, wherein the first bridge terminal further comprises a first dome convex upwardly from the first bridge terminal and disposed around the first bezel-side through-hole.

6. The steering wheel according to claim 2, wherein the first contact projection directly contacts the first contact.

7. The steering wheel according to claim 1, wherein the second PCB has a second contact having a disk shape, and
    wherein the second conductive bezel has a second contact projection, which has a shape extending from an edge of the second conductive bezel and is spaced apart from the second PCB, electrically connected to the second contact.

8. The steering wheel according to claim 7, wherein the second contact projection is electrically connected to the second contact through a second bridge terminal.

9. The steering wheel according to claim 8, wherein the second bridge terminal comprises:
    a second bezel-side through-hole defined to be aligned with the second contact projection;
    a board-side through-hole defined to be aligned with a through-hole of the second contact;
    a second bezel-side screw configured to pass through the second bezel-side through-hole and the second contact projection; and
    a board-side screw configured to pass through the board-side through-hole and the through-hole of the second contact.

10. The steering wheel according to claim 7, wherein the second contact projection directly contacts the second contact.

11. The steering wheel according to claim 1, wherein the signal processor is coupled to the first PCB.

12. The steering wheel according to claim 1, further comprising:
    an armature to which the hub, the plurality of spokes, and the rim are connected as a center of the steering wheel; and
    a bottom member arranged under the armature,
    wherein the first and second conductive bezels are attached to a top surface of the armature,
    wherein the bottom member is attached to a bottom surface of the armature,
    wherein the first and second conductive bezels are connected to the armature together with the bottom member through a plurality of screws, and
    wherein the bottom member includes an insulating material.

13. The steering wheel according to claim 12, further comprising a cylindrical member detachably coupled to each of the first and second conductive bezels,
    wherein the cylindrical member includes an insulating material,
    wherein the cylindrical member is interposed between each conductive bezel and the armature, and
    wherein each of the plurality of screws is configured to be screwed into the cylindrical member.

14. The steering wheel according to claim 13, wherein the armature has a through-hole through which each screw passes,
    wherein the bottom member has a through-hole through which the screw passes, and
    wherein the through-hole of the armature and the through-hole of the bottom member have a diameter greater than that of the screw.

15. The steering wheel according to claim 14, wherein the cylindrical member has a pair of first coupling protrusions spaced apart from each other by a predetermined gap, and
    wherein each conductive bezel has an insertion protrusion extends through the gap between the pair of first coupling protrusions.

16. The steering wheel according to claim 15, wherein each conductive bezel has a pair of support walls spaced apart from each other,
    the pair of support walls are spaced apart from each other by a gap corresponding to a diameter of the cylindrical member,
    wherein each support wall has a coupling hole,
    wherein the cylindrical member has a pair of second coupling protrusions disposed to be opposite to each other,
    wherein the pair of second coupling protrusions protrude from an exterior surface of the cylindrical member such that the pair of second coupling protrusions are perpendicular to the pair of first coupling protrusions, and
    wherein each second coupling protrusion extends through the coupling hole of the corresponding support wall.

17. The steering wheel according to claim 12, wherein each conductive bezel has a cylindrical portion extending toward the armature,
    wherein the cylindrical portion passes through a through-hole of the armature, and
    wherein each screw passes through the bottom member and is configured to be screwed into the cylindrical portion.

18. The steering wheel according to claim 17, wherein an insulating layer is coupled to an exterior surface of the cylindrical portion.

\* \* \* \* \*